United States Patent [19]

Someya

[11] Patent Number: 4,619,473
[45] Date of Patent: Oct. 28, 1986

[54] FLUID PASSAGE CONNECTOR FOR LIQUID CHROMATOGRAPH

[75] Inventor: Noboru Someya, Chiba, Japan

[73] Assignee: Tokyo Rika Kikai Co., Ltd., Japan

[21] Appl. No.: 600,784

[22] Filed: Apr. 16, 1984

[30] Foreign Application Priority Data

Apr. 18, 1983 [JP] Japan ................................. 58-68212

[51] Int. Cl.⁴ ............................................. F16L 25/00
[52] U.S. Cl. .................................... 285/353; 285/352; 285/369; 285/334.3; 285/174; 285/383
[58] Field of Search .............. 285/353, 352, 369, 383, 285/334.3, 174

[56] References Cited

U.S. PATENT DOCUMENTS

| | | | |
|---|---|---|---|
| 731,348 | 6/1903 | Eshelman | 285/353 X |
| 1,033,196 | 7/1912 | Roesch | 285/353 X |
| 2,805,873 | 9/1957 | Brennan et al. | 285/353 X |
| 4,165,893 | 8/1979 | Fields | 285/352 X |

Primary Examiner—Richard J. Scanlan, Jr.
Attorney, Agent, or Firm—Wegner & Bretschneider

[57] ABSTRACT

A fluid passage connector for liquid chromatographs, which comprises a tube having a flat portion at one end, a bushing fixed to the outer periphery of said tube, a joint having therethrough a fluid passage, around the opening portion of which is provided a seal seat surface, and an engaging member for urging the bushing for said tube, which is inserted into said joint, thereby to fluid-tightly engage the flat end portion of said tube with said seal seat surface.

13 Claims, 11 Drawing Figures

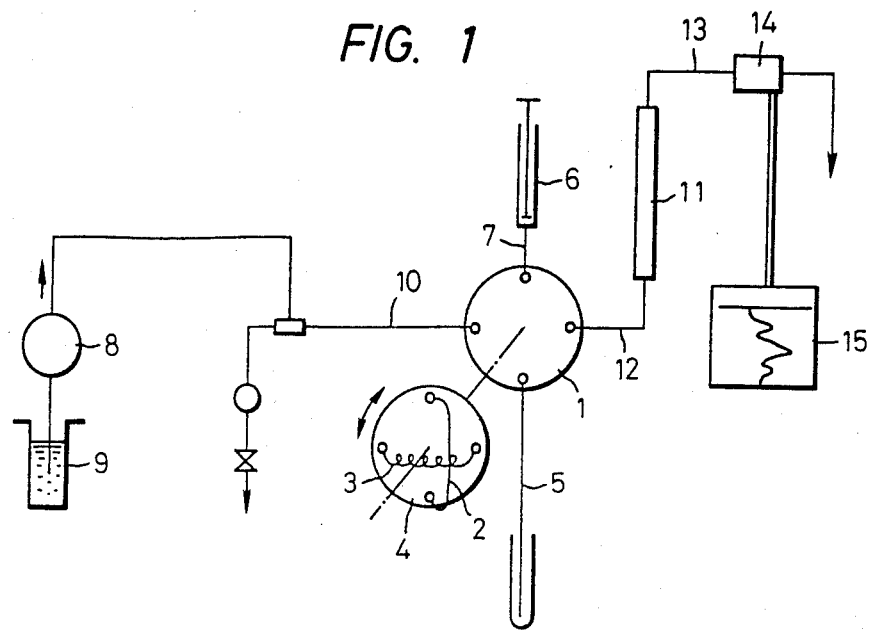
FIG. 1
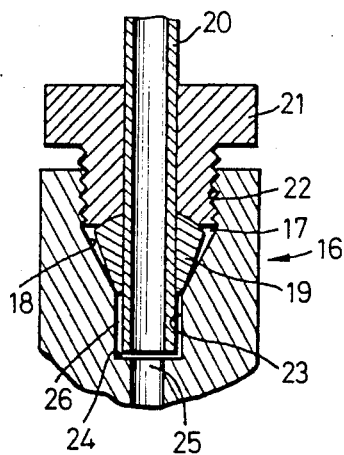
PRIOR ART
FIG. 2
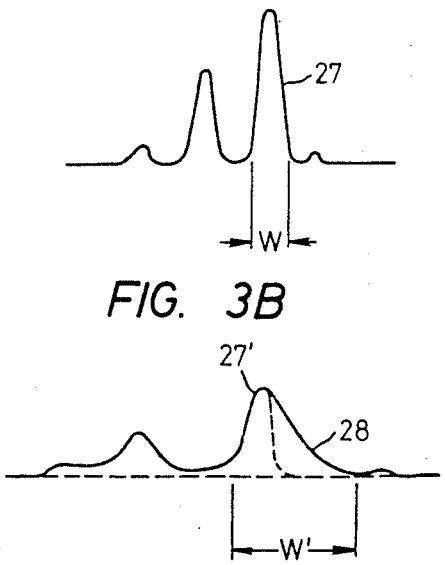
FIG. 3A
FIG. 3B

FLUID PASSAGE CONNECTOR FOR LIQUID CHROMATOGRAPH

FIELD OF THE INVENTION

The present invention relates to a fluid passage connector for piping or tubing used with liquid chromatographs, in particular high-speed liquid chromatographs and the like.

BACKGROUND OF THE INVENTION

The conventional fluid passage connectors for such tubing are typically of the type that a connecting opening formed in the main body of a metallic joint is partly tapered inwardly, and said inwardly tapered portion is engaged in a fluid-tight manner with a holder member fixed in the vicinity of the end of a tube to be connected, i.e., a metallic ferrule in a conical and ring-like form, with the use of an engaging member such as a push bolt for the sealing purpose.

For example, FIG. 1 is a view illustrative of the arrangement of a typical analyzer, in which a sample inject valve 1 is connected to a movable sample inject valve 4 having sample reservoir loops 2 and 3, and is further connected to with a sample intake tube 5 and a connecting tube 7 for suction means 6 at diametrically opposed positions. The arrangement also has a solvent supply tube 10 leading to a solvent reservoir 9 equipped with a solvent supply pump 8, and a connecting tube 12 for a column 11 at diametrically opposed positions, column 11 is connected with a UV-ray absorbing monitor 14 by way of a tube 13. Furthermore, the monitor 14 is electrically connected with a recorder 15 to record data.

As shown in FIG. 2, the conventional fluid passage connector for tubing used with such a chromatograph is typically of the type that a connecting opening 17 formed in the main body 16 of a metallic joint is partly provided with an inwardly tapered face 18, a tube 20 is inserted through a push bolt 21, said tube 20 being fixedly provided with a metallic ferrule 19 in the vicinity of the lower end thereof, said ferrule 19 combining a tube holding member with a sealing member, and the push bolt 21 is engaged with an internally threaded portion 22 of said connecting opening 17, followed by clamping with a large torque with the use of a tool such as a wrench, whereby the end edge of the ferrule 19 is engaged with the tapered face 18 of said connecting opening 17 for sealing.

Moreover, the tube 20 is fitted at its end into the deepest space 23 of the connecting opening 17, and a fluid passage 25 is open at the bottom 24 of the tube 20. In addition, the end portion of the tube 20 slightly projects from the end portion of the metallic ferrule 19. Furthermore, it is impossible to exclude completely the tube fitting space 23 between the deepest portion of the connecting opening 17 and the top of tube 20. In consequence, there is formed a gap 26 around the end of the tube 20. A sample molecule or solvent diffuses into or out from that gap 26 during analysis, thus forming a dead volume and posing a grave bar to an efficient separation. When it is desired to obtain as a result of accurate analysis a chart having a separation peak 27 of a normal width W, as shown in FIG. 3(A), it is likely that the width W' of a separation peak 27' may become wide, as shown in FIG. 3 (B), tailing 28 may take place, leading to unsatisfactory separation, and the height of a peak may vary, resulting in the base line being unreliable. Thus, the prior art is disadvantageous in that no accurate analytical data of good reproductivity are obtained. Such a disadvantage becomes further marked, when there are an increasing number of connections.

It is further required to hold the push bolt 21 in place with a greater torque by screwing or other means, since sealing is effected with the metallic ferrule 19 and the tapered face 18 of the main body 16 of the metallic joint. This needs a special tool such as a wrench. The application of a still greater torque to screw the bolt 21 in place may cause deformation of the tube 20 and, hence, a reduction in the cross-sectional area of the fluid passages 25. Thus, the prior art is unsuitable for use in the connection of flexible tubes.

From now on, there will be an increasing tendency toward the use of highly sensitive microanalysis, and the presence of a dead volume in each joint will cause a further important problem.

SUMMARY OF THE INVENTION

In order to achieve the aforesaid objects, the first aspect of the present invention provides a fluid passage connector for liquid chromatographs, which comprises a tube having a flat portion at one end, a retainer member fixed to the outer periphery of said tube, a joint having therethrough a fluid passage, around the opening portion of which is provided a seal seat surface, and an engaging member for urging the retainer member for said tube, which is inserted into said joint, thereby to fluid-tightly engage the flat end portion of said tube with said seal seat surface.

The second aspect of the present invention is characterized in that, in the first aspect of the present invention, the flat end portion of said tube is engaged with said seal seat surface through a packing.

The third aspect of the present invention is characterized in that, in the first aspect of the present invention, the flat end portion of said tube is engaged directly with said seal seat surface.

The fourth aspect of the present invention is characterized in that, in the second aspect of the present invention, said seal seat surface is defined by a packing to be fitted to said tube having a flat portion at one end.

The fifth aspect of the present invention is characterized in that, in the first, second, third or fourth aspect of the present invention, said tube is formed of stainless steel.

The sixth aspect of the present invention is characterized in that, in the first, second, third or fourth aspect of the present invention, said tube is formed of a synthetic resin.

According to the present invention, this object is achieved by the provision of a liquid chromatograph wherein a tube is fluid-tightly connected to a connecting opening having a fluid passage by urging a tube holder member with the use of urging or engaging means, characterized in that the flat end portion of said tube is fluid-tightly engaged with a sealing seat face formed around the open portion of said fluid passage.

BRIEF DESCRIPTION OF THE DRAWINGS

The present invention will become apparent from the following detailed description with reference to the accompanying drawings, in which:

FIG. 1 is a view showing one typical example of liquid chromatographs,

FIG. 2 is a sectional view showing the prior art tube connector arrangement,

FIGS. 3A and 3B are charts obtained with the use of the liquid chromatograph, and, FIGS. 4 to 10 inclusive are sectional views showing various embodiments of the fluid passage connector for tubing according to the present invention.

DETAILED DESCRIPTION OF THE PREFERRED EMBODIMENTS OF THE INVENTION

The fluid passage connector of the present invention will now be explained in detail with reference to the embodiments of FIGS. 4 to 10 inclusive.

Figure 4:
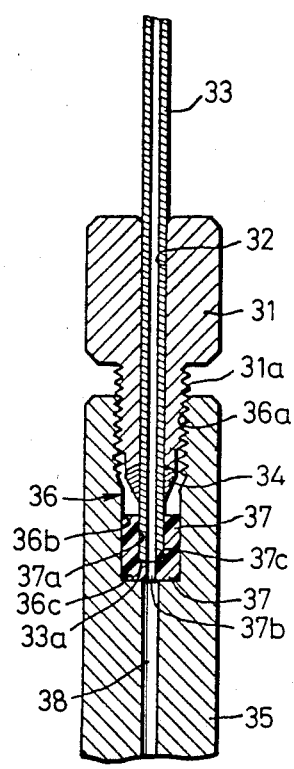

FIG. 4 illustrates one embodiment of the tube connector according to the present invention, which is applicable to the connection of a tube 33 of stainless steel. The tube 33 is inserted through a through-hole 32 axially formed in a push bolt or engaging member 31, and is fixedly provided in the vicinity of the end thereof with a ferrule 34 of stainless steel, which functions as a holder member for the tube 33. The end portion of the tube 33 is formed into a flat portion 33a by cutting it perpendicularly to the axial direction.

A connecting opening 36 formed in a metallic joint 35 is internally threaded at 36a for engagement with a threaded portion 31a of the push bolt 31. A cylindrical packing 37 of synthetic resin is provided at a portion 36b adjacent to the internally threaded portion 36a of the opening 36. This packing 37 includes a recess 37a for receiving the tube, a fluid passage 37b contiguous thereto, and a sealing seat face 37c formed around said passage 37b. The bottom 36c of the opening 36 serves as a seal seat surface and is formed in the center with a passage 38 in communication with fluid passage 37b.

To make connection with respect to the tube with a given pressure-resistant sealing force by the thus arranged joint, the side of the head of the push bolt 31 is screwed manually so that the bolt 31 is threadedly inserted through the connecting opening 36 with its end being engaged with the ferrule 34 fixed to the tube 33. Further threaded insertion of the bolt 31 causes the tube 33 to advance in the opening 36, so that the end portion of the tube 33 first fits into the recess 37a in the packing 37. Further advancement of the tube causes it engage at its flat end portion 33a with the sealing seat face 37c of the packing 37 for sealing. Having a certain degree of elasticity, the cylindrical packing 37 comes into close contact with the bottom 36c of the opening 36, and further bulges out, so that the inner face of the opening 36 is also fluid-tightly connected with the outer face of the end portion of the tube 33.

In this manner, only the fluid passage 37b is formed without formation of any dead volume at the end portion of the tube 33, and is in communication with the fluid passage 38 in the main body 35 of the joint.

Figure 5:
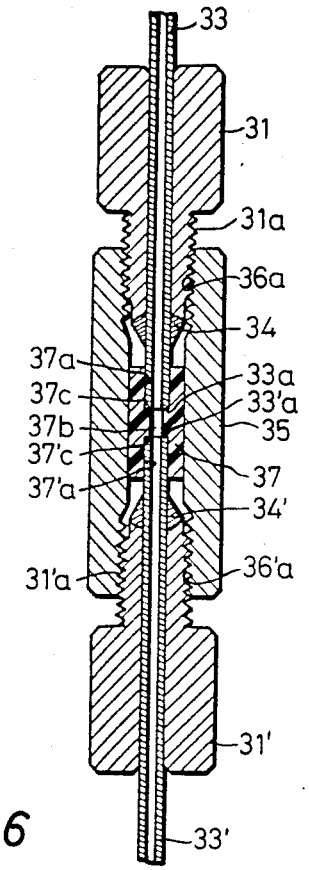

FIG. 5 is a view showing one embodiment of the fluid passage connector used for connecting two tubes. A joint 35 includes a connecting opening 36 extending axially therethrough, and has a cylindrical packing 37 provided in the center.

The connecting opening 36 is internally threaded at 36a and 36'a on the inner edges of both its open portions, whilst the cylindrical packing 37 includes in both its end faces recesses 37a and, 37'a for receiving the tube and a passage 37b for making communication between both recesses 37a and 37'a.

Referring to tubes 33 and 33' of stainless steel. to be connected together with this joint 35, they are inserted through push bolts 31 and 31', and are fixed in the vicinity of their end portions with ferrules 34 and 34' of stainless steel. Both tubes 33 and 33' are fitted at their end portions into the recesses 37a and 37'a and both push bolts 31 and 31' are engaged at their externally threaded portions 31a and 31'a with the externally threaded portions 36a and 36'a. Subsequent advancement of both tubes 33 and 33' causes that their flat end portions 33a and 33'a are engaged with the sealing seat faces 37c and 37'c of the cylindrical packing 37 for the achievement of fluid-tight sealing with no formation of any dead volume.

Figure 6:
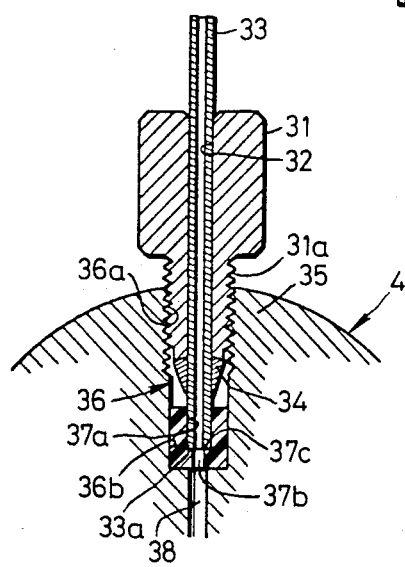

FIG. 6 illustrates one embodiment for connecting a tube to valve means. A joint 35 is characterized in that it constitutes a part of the valve means. Connection can be made in the same manner as described with reference to FIG. 4.

Figure 7:
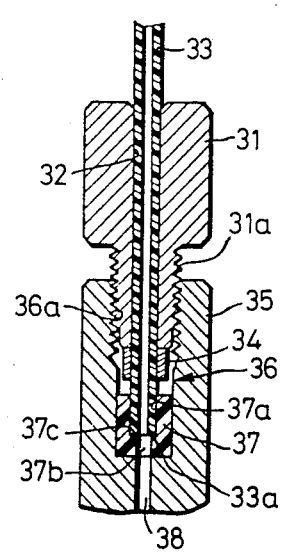

FIG. 7 is a view showing one embodiment of a joint for a flexible tube, to which is fixed a ring-like ferrule 34 functioning as a holder member for preventing disengagement of a flexible tube of synthetic resin such as of silicone or Teflon. A metallic ferrule is fixed to a metallic tube by caulking with a greater force. If such a ferrule is attached to the flexible tube, then it will collapse. This is because, in this embodiment, a pipe-like metallic ring is provided therein with a single slit fixedly fitted over the end portion of the tube in place by caulking using a tool. The action of this embodiment is identical with that of FIG. 4.

Figure 8:
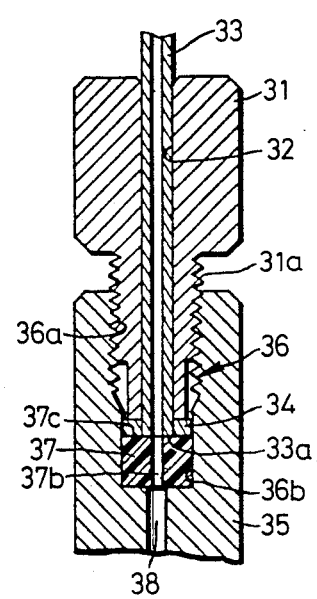

FIG. 8 illustrates an embodiment in which a collar-like ferrule is attached to the end portion of a tube. The collar-like ferrule 34 is fixed to the end portion of a tube 33 with its end face being flush with the flat end face of the tube 33, whilst a cylindrical packing 37 is provided with a planar sealing seat face 37 with no formation of any recess. The flat end face 33a of the tube 33 mounted in a connecting opening 36 and the end face of the ferrule 34 are engaged with the sealing seat face 37c for fluid-tight sealing, thereby preventing any dead volume from being formed.

Figure 9:
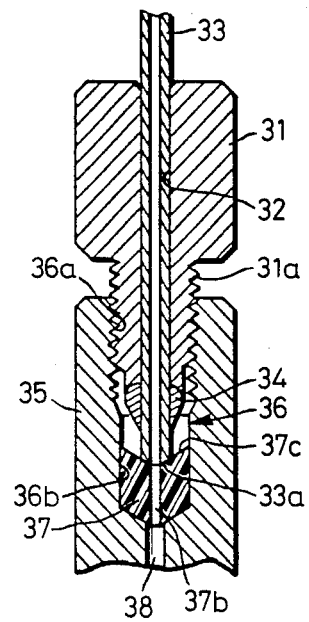

FIG. 9 is a view showing one embodiment wherein a tube is tapered at the end portion. A tube 33 is tapered on the flat end portion 33a. Tapering is effected with respect to a sealing seat face 37c of a cylindrical packing 37, with which the flat end face 33a is engaged. Further, tapering is effected with respect to the bottom of a connecting opening 36 and the end face of the packing 37, which engages the same.

Figure 10:
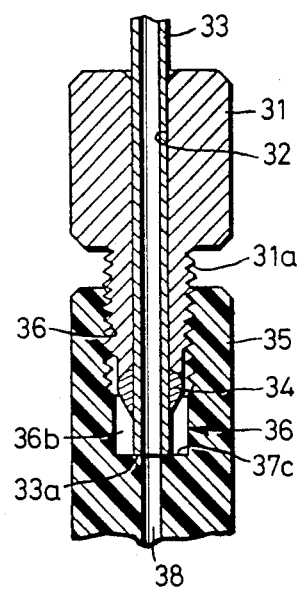

In the embodiment illustrated in FIG. 10, no use is made of any cylindrical packing. A joint is formed of an elastic material such as synthetic resin. A connecting opening 36 is provided on the bottom with a sealing seat face 37c, with which the flat end face 33a of a tube 33 is engaged for fluid-tight sealing.

It is to be noted that assembling is further facilitated by knurling the outer face of the head of the push bolt 31.

As mentioned above, the flat end face of a tube is engaged with the sealing seat face formed around a passage for sealing. Thus it is possible to effect accurate analysis works with no formation of any dead volume. In addition, engagement with the end face of a tube makes it possible to obtain given pressure resistant sealing, even when the engaging means is used with a relatively small force. The present invention is also applicable to the connection of flexible tubes with no need of using any tool such as a spanner.

In addition to the aforesaid effect, a sufficient sealing effect is obtained, even when a clamping torque exerted by the push bolt is small. It is thus unlikely that the tube or tube joint may suffer deformation, scratches or break-down. This enables to re-use the tube or tube joint only by replacement of the cylindrical packing. For use, the tube may be cut into suitable length with no need of applying special processings.

While the present invention has been described with reference to the specific embodiments, it is to be understood that the invention is not limited thereto, and many changes or modifications may be made without departing from the scope defined in the appended claim.

What is claimed is:

1. A fluid passage connector for liquid chromatographs comprising a push bolt having a threaded portion at one end thereof and an axial hole therethrough; a tube extending through said axial hole, with the end of said tube extending through said hole, and proximate said threaded portion, being flat; a ferrule surrounding said tube near end thereof and abutting said one end of said push bolt; a cylindrical packing member having an axial recess at one end thereof terminating in a shoulder and having an axial passage therethrough; said end of said tube being seated in said axial recess against said shoulder; and a joint member having an axial opening therein terminating in a shoulder, at least a portion of the wall surrounding said opening distal from said last-mentioned shoulder being threaded, and an axial passage therethrough; said cylindrical packing member being seated in said axial opening against said last-mentioned shoulder; said threaded portion of said push bolt being inserted in said axial opening and threadedly engaged therewith; whereby a fluid-tight joint is produced.

2. A fluid passage connector as defined in claim 1, wherein said tube and said axial passages together form a continuous fluid passage having a substantially uniform diameter.

3. A fluid passage connector as defined in claim 1, in which the flat end portion of said tube is engaged with a seal seat surface in said cylindrical packing.

4. A fluid passage connector as defined in claim 1, in which the flat end portion of said tube is engaged directly with a seal seat surface.

5. A fluid passage connector as defined in claim 3, in which said seal seat surface is defined by said cylindrical packing to be fitted to said tube having a flat portion at one end.

6. A fluid passage connector as defined in claim 1, in which said tube is formed of stainless steel.

7. A fluid passage connector as defined in claim 3, in which said tube is formed of stainless steel.

8. A fluid passage connector as defined in claim 4, in which said tube is formed of stainless steel.

9. A fluid passage connector as defined in claim 5, in which said tube is formed of stainless steel.

10. A fluid passage connector as defined in claim 1, in which said tube is formed of synthetic resin.

11. A fluid passage connector as defined in claim 3, in which said tube is formed of synthetic resin.

12. A fluid passage connector as defined in claim 4, in which said tube is formed of synthetic resin.

13. A fluid passage connector as defined in claim 5, in which said tube is formed of synthetic resin.

* * * * *